(12) United States Patent       (10) Patent No.: US 9,700,235 B2
Baker et al.                          (45) Date of Patent:     Jul. 11, 2017

(54) PEAK EXPIRATORY FLOW RATE MEASUREMENT APPARATUS

(71) Applicants: Jeff Baker, Orlando, FL (US); Mark Bunker, Orlando, FL (US); Paul van der Pol, Winter Garden, FL (US)

(72) Inventors: Jeff Baker, Orlando, FL (US); Mark Bunker, Orlando, FL (US); Paul van der Pol, Winter Garden, FL (US)

(73) Assignee: Noble International, Inc., Orlando, FL (US)

( * ) Notice: Subject to any disclaimer, the term of this patent is extended or adjusted under 35 U.S.C. 154(b) by 532 days.

(21) Appl. No.: 13/668,578

(22) Filed: Nov. 5, 2012

(65) Prior Publication Data

US 2013/0123655 A1    May 16, 2013

Related U.S. Application Data

(60) Provisional application No. 61/555,143, filed on Nov. 3, 2011.

(51) Int. Cl.
    *A61B 5/087*        (2006.01)
(52) U.S. Cl.
    CPC ................. *A61B 5/0871* (2013.01)
(58) Field of Classification Search
    CPC .................................. A61B 5/0871
    See application file for complete search history.

(56) References Cited

U.S. PATENT DOCUMENTS

| 5,224,487 A * | 7/1993 | Bellofatto | A61B 5/0871 128/200.24 |
| 5,839,430 A * | 11/1998 | Cama | A61B 5/0871 128/200.14 |
| 7,390,305 B2* | 6/2008 | Nuttall | A61B 5/0871 600/529 |
| 2006/0217627 A1* | 9/2006 | Nuttall | 600/538 |
| 2007/0239058 A1* | 10/2007 | Krasilchikov | A61B 5/087 600/538 |

* cited by examiner

*Primary Examiner* — Meredith Weare
(74) *Attorney, Agent, or Firm* — Timothy H. Van Dyke; Beusse, Wolter, Sanks & Maire PLLC

(57) ABSTRACT

A peak expiratory flow rate measuring apparatus (PFM) having at least one measurement channel and at least one bypass flow channel including at least one entrance, at least one exit, at least an inner wall and an outer wall, and wherein at least a portion of said at least one bypass flow channel has a variable cross-sectional area, is provided herein. Further disclosed is a PFM having at least one measurement channel comprising at least one first flow entrance, at least one bypass flow channel comprising at least one second flow entrance, and at least one guide wall, having an axially forward portion adjacent to the second flow entrance and an axially aft portion adjacent to the first flow entrance is provided.

7 Claims, 2 Drawing Sheets

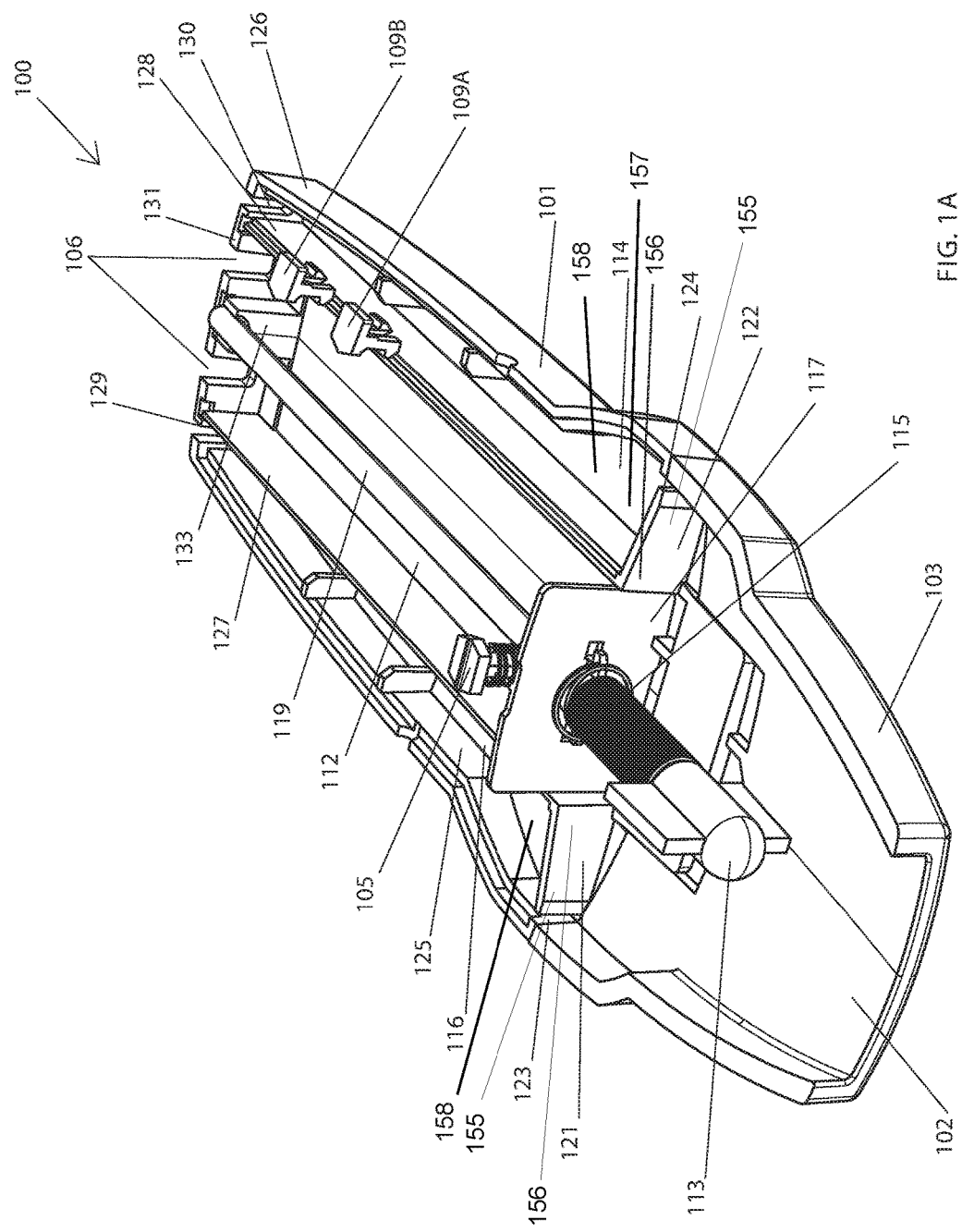

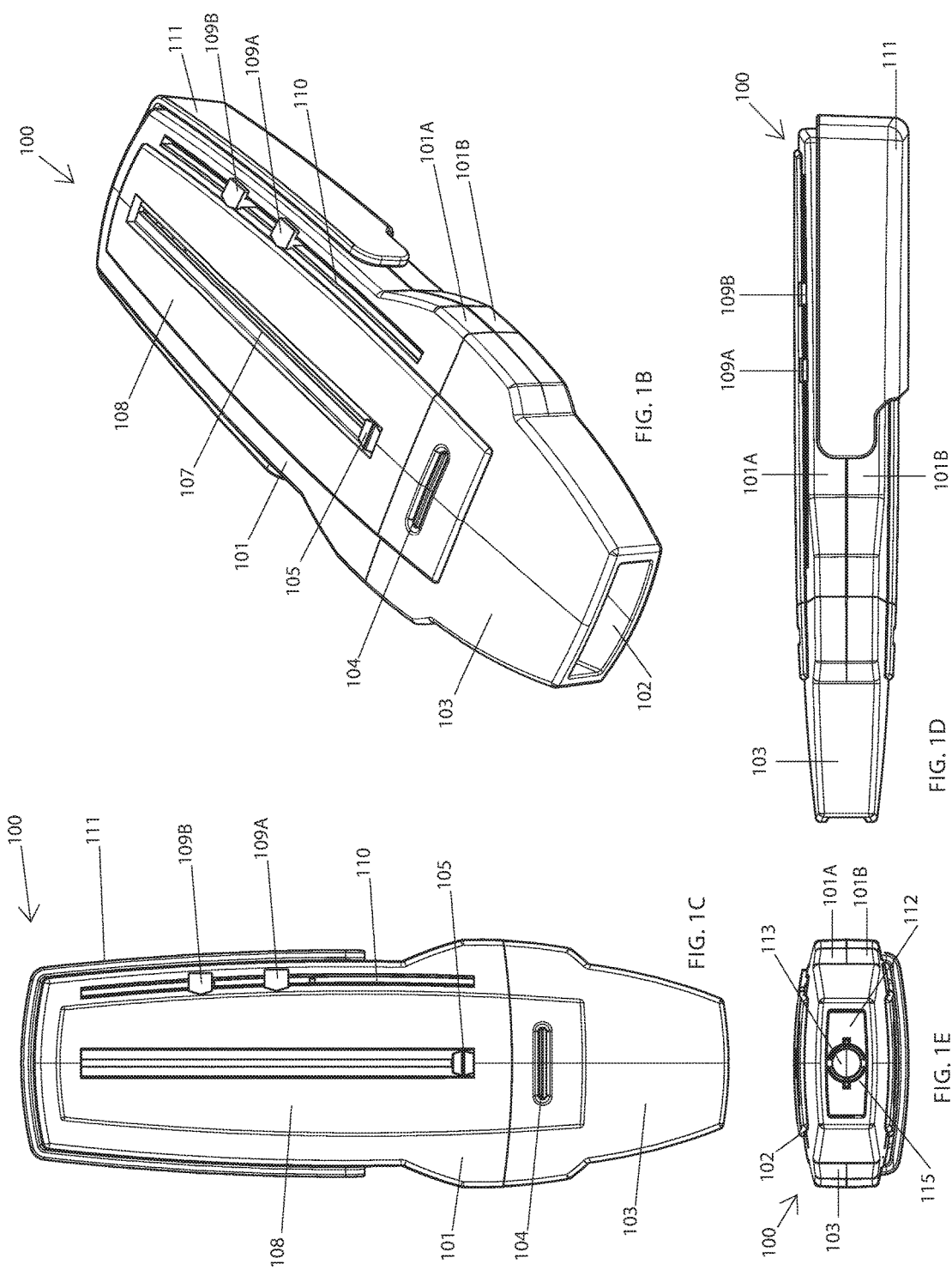

PEAK EXPIRATORY FLOW RATE MEASUREMENT APPARATUS

CROSS REFERENCE TO RELATED APPLICATIONS

This application claims priority to U.S. Provisional Application Ser. No. 61/555,143 filed Nov. 3, 2011, which is incorporated herein by reference in its entirety.

FIELD

At least some embodiments relate to flow measuring devices, more specifically to medical devices for measuring peak expiratory flow (PEF) rates of lungs and bronchial tubes.

SUMMARY

Herein disclosed is a peak expiratory flow rate measuring apparatus (PFM) having at least one measurement channel and at least one bypass flow channel comprising at least one entrance, at least one exit, at least an inner wall and an outer wall, and wherein at least a portion of said at least one bypass flow channel has a variable cross-sectional area.

Further disclosed is a PFM having at least one measurement channel comprising at least one first flow entrance, at least one bypass flow channel comprising at least one second flow entrance, and at least one guide wall, having an axially forward portion adjacent to said second flow entrance and an axially aft portion adjacent to said first flow entrance.

Still further disclosed is a PFM comprising at least one measurement channel having at least one first flow entrance, at least one bypass flow channel having at least one second flow entrance, wherein at least a portion of said at least one bypass flow channel comprises a variable cross-sectional area, and at least one guide wall, comprising an axially forward portion adjacent to said second flow entrance and an axially aft portion adjacent to said first flow entrance.

BRIEF DESCRIPTION OF THE DRAWINGS

Some embodiments are better understood by reading the following Detailed Description, taken together with the Drawings, wherein:

FIG. 1A is a cutaway view of an embodiment of a PFM in accordance with this Disclosure;

FIG. 1B is a perspective view of an embodiment of a PFM in accordance with this Disclosure;

FIG. 1C is a top down view of an embodiment of a PFM in accordance with this Disclosure;

FIG. 1D is a side view of an embodiment of a PFM in accordance with this Disclosure; and FIG. 1E is a front view looking into an opening of an embodiment of a PFM in accordance with this Disclosure.

DETAILED DESCRIPTION

Disclosed embodiments in this Disclosure are described with reference to the attached figures, wherein like reference numerals are used throughout the figures to designate similar or equivalent elements. The figures are not drawn to scale and they are provided merely to illustrate the disclosed embodiments. Several aspects are described below with reference to example applications for illustration. It should be understood that numerous specific details, relationships, and methods are set forth to provide a full understanding of the disclosed embodiments. One having ordinary skill in the relevant art, however, will readily recognize that the subject matter disclosed herein can be practiced without one or more of the specific details or with other methods. In other instances, well-known structures or operations are not shown in detail to avoid obscuring structures or operations that are not well-known. This Disclosure is not limited by the illustrated ordering of acts or events, as some acts may occur in different orders and/or concurrently with other acts or events. Furthermore, not all illustrated acts or events are required to implement a methodology in accordance with this Disclosure.

Notwithstanding that the numerical ranges and parameters setting forth the broad scope of this Disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein.

In at least some embodiments, a peak expiratory flow rate measuring apparatus (PFM) is disclosed. FIG. 1A shows a cutaway view of at least one embodiment of a PFM in accordance with this Disclosure. FIGS. 1B, 1C, 1D, and 1E show different views of at least one embodiment of a PFM having its covering disposed thereon.

Referring to FIG. 1A, a PFM 100 may have a shell 101 comprising at least one piece of continuous material. The shell 101 may have one or more holes portions of removed material, or holes formed in the shell 101. The shell 101 may have multiple sections. For example, referring to FIGS. 1B, 1D and 1E, the shell 101 may comprise at least two sections such as but not limited to a first shell portion 101A and a second shell portion 101B.

Referring back to FIG. 1A, at least some embodiments of a PFM may have a measurement channel 112. The at least one measurement channel 112 may be a cavity being formed inside at least one wall of any shape and having a cross-section. The measurement channel 112 may have any cross-sectional shape. In at least some embodiments, at least one cross-section of a measurement channel may have a shape including but not limited to, a square, rectangle, or a circle.

The measurement channel 112 may be defined by at least a portion of shell 101 and at least a portion of a first inner wall 128. The measurement channel may also be defined by at least a portion of a second inner wall 127. In at least some embodiments, the measurement cavity 112 is a rectangular cavity having a width of about 23 mm, a height of about 16 mm, and a length of about 85 mm.

The measurement channel 112 may terminate at an end 131 having at least one exit hole 106. The end 131 may be at least a portion of the shell 101, or a separate piece formed integrally upon the shell 101, or a separate piece attached to the shell 101 in any manner suitable, or any combination thereof. The at least one exit hole 106 may be of any shape and have a total area of about 81 $mm^2$. The end 131 may have at least two exit holes 106.

The end 131 may be configured to accept at least one slider rod 119 in at least a portion of the end 131. At least one protrusion 133 may further accept the at least one slider rod 119 and act as support. The at least one protrusion 133 may be at least a portion of the shell 101 or end 131, or a separate piece formed integrally upon the shell 101 or end 131, or a separate piece attached to the shell 101 or end 131 in any manner suitable, or any combination thereof.

A blow plate 117 may be disposed on the at least one slider rod 119 such that the blow plate 117 is slidably connected to the at least one slider rod 119. The blow plate 117 may be of any size and shape. In at least some embodiments, the shape of the blow plate 117 approximates the shape of the measurement channel 112 such that the blow plate 117 may slide into and out of the measurement channel 112.

The blow plate 117 may have dimensions that are slightly smaller than the borders of the measurement channel 112 so that there is a small gap between the walls of the measurement channel 112 and the blow plate edges. This may allow an air flow to pass around the blow plate if desired.

The blow plate 117 may push at least one measuring device 105 to a position in the measurement channel 112. Referring to FIGS. 1A, 1B and 1C, the measuring device 105 may slide along a measuring slit 107. The measuring device 105 may be of such a shape that may hang into the measuring slit 107 and be pushed by the blow plate 117 when the blow plate moves along the measurement channel 112 toward the end 131. A portion of the measuring device 105 may slide along the at least one slider rod 119 and have a spring 115 or other device securing the measuring device 105 to the first shell portion 101A.

The measuring slit 107 may be a portion of removed material from at least a portion of the first shell portion 101A and have any shape effective to allow the measuring device 105 slide with the blow plate 117 in at least a portion of the measurement channel 112. The slit may have a rectangular shape and have the dimensions of 1.5 mm wide by 82 mm long.

The measurement slit 107 and the measuring device 105 may be disposed on a portion of the shell 101 where at least one scale is disposed upon. At least one scale face 108 may be disposed upon the shell 101 or a first shell portion 101A next to the measurement slit 107 and measuring device 105 such that the position of the measuring device 105 along the measurement slit 107 corresponds to a value on at least one scale disposed on the scale face 108.

The scale face 108 may have a scale that corresponds the position of the measuring device 105 to a flow rate. Using such a scale and at least some features as described above, the PFM may measure the maximum flow rate exerted on the blow plate 117, otherwise known as the peak expiratory flow rate (PEFR). Determining the PEFR of a person blowing into the PFM can help determine the condition of that person's respiratory system. The at least one scale may read Liters per minute. The scale for an adult PFM typically ranges from about 60 L/min to about 800 L/min. The scale for a pediatric PFM typically ranges from about 50 L/min to about 400 L/min.

At least one spring 115 may be attached to a blow plate 117 either permanently or removably. The spring may act to pull the blow plate 117 back to an initial position. The spring 115 may have a spring rate and dimensions selected to provide a desired force. The desired force may be such that a person blow on the blow plate 117 and the blow plate would move along the at least one slider rod 119 in the direction of the end 131 enough that the amount of movement of the plate could be determined and compared to a scale of flow rates. The stiffer the spring 115, the faster the airflow hitting the blow plate 117 would have to be to move the blow plate the same distance. The dimensions of the spring for medical diagnostic purposes may be 15 mm long (without load), 7 mm in diameter, and has a spring rate of 0.0045 kg/mm.

At least some embodiments of a PFM may have at least one bypass flow channel. A bypass flow channel may be, for example but not limited to, a first bypass flow channel 114 or a second bypass flow channel 116. The at least one bypass flow channel may have at least one entrance opening, at least one inner wall, at least one outer wall, and at least one exit opening. The size and shape of the openings may affect the airflow into and out of the bypass channels. The area of the entrance (123 or 124) is approximately 40 mm$^2$ per channel. The area of the exit opening (129 or 130) is approximately 19 mm$^2$ per channel.

The at least one inner wall may be of any shape. In at least some embodiments, the at least one inner wall may form at least a portion of the measuring channel on a first side and at least a portion of the at least one bypass channel on a second side. In at least some embodiments, the at least one inner wall is flat and straight from beginning to end on both sides and 112 as well. In other embodiments, the first side of the inner wall that communicates with the measuring channel may be flat and straight while the second side that communicates with the bypass channel may have a variable shape. A variable shape may be any shape of a wall that is effective to create a variable cross-section in a direction of flow for example. Examples of a variable shape may be, but are not limited to, non-linear shapes such as concave shapes and convex shapes, linear angled shapes, and combinations thereof. Such non-linear shapes may be parabolic for example.

The at least one outer wall may be formed by or attached on at least a portion of the shell 101. In some embodiments the at least one outer wall may have a first side that communicates with at least one bypass channel and a second side that communicates with either the shell 101 or the surroundings. The first side may have a variable shape such as a reducing or expanding shape that would act to narrow or expand the at least one bypass flow channel. The second side may be any shape, such as flat and constant or curved and variable. A variable shape may be any shape of a wall that is effective to create a variable cross-section in a direction of flow for example. Examples of a variable shape may be, but are not limited to, non-linear shapes such as concave shapes and convex shapes, linear angled shapes, and combinations thereof. Such non-linear shapes may be parabolic for example.

Using walls as described above, the at least one bypass flow channel may have a non-constant shape. For example, at least a portion of the at least one bypass flow channel may act as a reducer. In some embodiments, at least a portion of the bypass flow channel may act as an expansion chamber. The change in the shape of the at least one bypass flow channel may be linear or non-linear.

The relationships between the spring rate, the at least one bypass channel characteristics including entry and exit sizes, the size of the measurement channel, blow plate, measuring slit and any other airflow exits determines the accuracy of and linearity (being defined as having equidistant spaces between the values on the scale) of the PFM. The relationships between the above elements can be established and tuned through experimentation and simulation using computational fluid dynamics software. In these experiments and simulations, three variables interact. These variables, a mix of air flow, air pressure, and spring rate, are dynamic over a fraction of a second, during which the subject's expiratory flow rate reaches its peak. As the subject's expiratory flow rate reaches its peak, the three variables fall into equilibrium and the blow plate stops moving forward. The duration to reach peak expiratory flow rate is between 35 and 170 milliseconds. The three variables are:
1. The force that pushes compressed air into the measurement channel, where it cannot escape, moving the blow plate forward and enlarging the volume in front of the blow plate.
2. The force that pushes compressed air through the bypass channels, lowering air pressure against the blow plate.
3. The force that stretches the spring, which is approximately linear over the distance the blow plate travels.

Considering that the spring rate (third variable) behaves approximately linearly, the two variables that are hard to established, because they do not behave linearly, are:
1. The enlargement rate of the volume in front of the blow plate as the displacement of the blow plate changes over time.
2. The air flow rate in the bypass channels. As the bypass channel is tapered, and the entrance hole is larger than the exit hole, the air flow in the bypass channel becomes constricted over time.

By creating experiments that carefully change the ratio of the rate of volume enlargement versus the rate of constriction in the bypass channels, then measuring the results on the scale of the PFM, the most desirable shapes and sizes can be established that result in the most accurate and linear response on the scale.

Referring to FIG. 1A, a first bypass flow channel 114 may comprise at least one first entrance 124, at least one first exit 130, a first inner wall 128, and a first outer wall 126. The second bypass flow channel 116 may comprise at least one second entrance 123, at least one second exit 129, at least a second inner wall 127 and a second outer wall 125. The PFM may have one or more bypass channels. Furthermore one or more bypass channels may have a variable cross-section to produce a reducing and/or expanding flow channel.

In embodiments where at least two bypass channels exist, the at least one first entrance 124 and at least one second entrance 123 may have the same or similar size and shape, or each may be different. Either may be at least one entrance opening as described above. The entrances may have an area of approximately 40 mm$^2$ per channel.

In embodiments where at least two bypass channels exist, the at least one first exit 130 and at least one second exit 129 may have the same or similar size and shape, or each may be different. Either may be at least one exit opening as described above. The exits may have an area of approximately 19 mm$^2$ per channel.

In embodiments where at least two bypass channels exist, the at least one first inner wall 128 and at least one second inner wall 127 may have the same or similar size and shape, or each may be different than the other. Either may be at least one inner wall as described above. The first inner wall 128 and the second inner wall 127 may have dimensions of 16 mm high and 94 mm long.

In embodiments where at least two bypass channels exist, the at least one first outer wall 126 and at least one second outer wall 125 may have the same or similar size and shape, or each may be different than the other. Either may be at least one outer wall as described above. The first outer wall 126 and the second outer wall 125 may have dimensions of 16 mm high and 95 mm long.

In some embodiments, a PFM may comprise at least one measurement channel as described above having a at least one first flow entrance, at least one bypass flow channel as described above comprising at least one second flow entrance, and at least one guide wall, having an axially forward portion 155 adjacent to said second flow entrance and an axially aft portion 156 adjacent to said first flow entrance. Such a guide wall may act as a flow director allowing flow to be directed toward the measuring channel.

The at least one guide wall may be formed on, or attached to at least a portion of the shell 101. The at least one guide wall may also be an extension of an inner wall as described above.

Referring to FIG. 1A, a first guide wall 122 and a second guide wall 121 are shown angled toward an entrance of the measurement channel 112 where the blow plate 117 may be positioned. The first and second guide walls may be a guide wall as described above. The first flow entrance may be any entrance to the measurement channel 112 that would allow air to enter into the measurement channel 112 or onto the blow plate 117. The second flow entrances may be an entrance as described above, such as a first entrance 124 or a second entrance 123. At least a portion of the guide walls may be flat and angled toward the measurement channel 112 as shown, or any other linear or non-linear shape effective to direct flow toward the measurement channel 112 and blow plate 117. FIG. 1A shows a bypass channel 114 with a variable cross-sectional area, wherein a cross-sectional area 158 adjacent to the second entrance 123, and distal to the second guide wall 121, for example, is larger than the cross-sectional area of the at least one second entrance 123. Therefore, an expansion chamber 157 is formed. Bypass flow channels 114, 116 are shown in FIG. 1A, wherein the bypass flow channels 114, 116 taper from the proximal end to the distal end of the PFM 100, forming a reducing flow channel.

In at least some embodiments, a PFM may have at least one bypass channel as described above and at least one guide wall as described above, as shown in the embodiment in FIG. 1A.

In at least some embodiments, a PFM has a mouthpiece 103. The mouthpiece may be attached to the shell 101 either removably or integrally, or possibly even be formed as an extension of the shell 101. The mouthpiece 101 may be one continuous piece of material or a conglomeration of multiple parts. The mouthpiece may have an entrance 102 and a vane structure 113 disposed in the mouthpiece 103. The mouthpiece 103 may be attached to an extension 104 of the shell 101 such the extension 104 communicates with at least a portion of a recess or hole in the mouthpiece 103 such that the extension 104 may hook onto the mouthpiece 103.

The vane structure 113 may be configured to accept an end of the slider rod 119 and to hold a spring 115 in place. The vane structure 113 may be integral upon the mouthpiece 103 or may be removably attached to the mouthpiece 103. For example, the mouthpiece 103 may have cut-outs form in the mouthpiece 103 that are configured to accept at least a portion of the vane structure 113.

In at least some embodiments, a PFM may have zone indicators 109. There may be an indicator for a red zone 109A, and one for a green zone 109B. The zone in between the green zone and the red zone is the yellow zone. A peak expiratory flow (PEF) reading in the green zone indicates that the respiratory condition is under good control. A PEF reading in the yellow zone indicates caution. It may mean respiratory airways are narrowing and additional medication may be required. A PEF reading in the red zone indicates a medical emergency. Severe airway narrowing may be occurring and immediate action needs to be taken. This would usually involve contacting a doctor or hospital. The treating physician sets the red, yellow, and green zones for the patient by sliding the zone indicators through channel 110.

The treating physician determines the zones based on the gender, age, height, respiratory condition, and drug regimen of the patient.

In at least one embodiment, a PMF may have a protective cap 111. While in use, this cap may rotate down such that it becomes a handle.

While various disclosed embodiments have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

Thus, the breadth and scope of the subject matter provided in this Disclosure should not be limited by any of the above explicitly described embodiments. Rather, the scope of this Disclosure should be defined in accordance with the following claims and their equivalents.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A peak expiratory flow rate measuring apparatus (PFM), comprising;
    at least one measurement channel comprising at least one first flow entrance;
    at least one bypass flow channel comprising a proximal end, a distal end, at least one second flow entrance at the proximal end, at least one exit at the distal end, at least one inner wall, at least one outer wall, and wherein at least a portion of said at least one bypass flow channel has a variable cross-sectional area; and
    at least one guide wall, having a proximal portion adjacent to said second flow entrance and said outer wall, and a distal portion adjacent to said first flow entrance and said inner wall, said guide wall being disposed between the inner wall and the outer wall, and angled toward the measurement channel to direct a flow toward the measurement channel,
    wherein the cross-sectional area of the bypass flow channel adjacent to the second flow entrance and distal to the guide wall is larger than a cross sectional area of the at least one second flow entrance, such that an expansion chamber is formed in the bypass flow channel, and the bypass flow channel tapers from a distal end of the expansion chamber to the distal end of the bypass flow channel, to form a reducing flow channel.

2. The PFM of claim 1 wherein said PFM comprises a non-linear change in said variable cross-sectional area from said at least one second flow entrance to said at least one exit.

3. The PFM of claim 1 wherein said PFM comprises a parabolic change in said variable cross-sectional area from said at least one second flow entrance to said at least one exit.

4. A peak expiratory flow rate measuring apparatus (PFM), comprising;
    at least one measurement channel comprising at least one first flow entrance;
    at least one bypass flow channel comprising a proximal end and a distal end, at least one second flow entrance at the proximal end and at least one exit at the distal end, wherein a cross sectional area of the at least one second flow entrance is smaller than a cross sectional area of the at least one first flow entrance; and
    at least one guide wall, having a proximal portion adjacent to said second flow entrance and a distal portion adjacent to said first flow entrance, said guide wall being angled toward the measurement channel to direct a flow toward the measurement channel, such that the at least one guide wall at least partially obstructs a portion of the bypass flow channel, such that a variable cross-sectional area of the bypass flow channel adjacent and distal to the second flow entrance is larger than a cross-sectional area of the at least one second flow entrance.

5. The PFM of claim 4, wherein said at least one guide wall comprises a linear shape.

6. The PFM of claim 4, wherein said at least one guide wall comprises a concave non-linear shape.

7. A peak expiratory flow rate measuring apparatus (PFM), comprising;
    at least one measurement channel having at least one first flow entrance;
    at least one bypass flow channel having a proximal end and a distal end, at least one second flow entrance at the proximal end and at least one exit at the distal end, wherein at least a portion of said at least one bypass flow channel comprises a variable cross-sectional area, wherein the variable cross-sectional area of the bypass flow channel adjacent and distal to the second flow entrance is larger than a cross sectional area of the at least one second flow entrance, forming an expansion chamber, and the bypass flow channel tapers from a distal end of the expansion chamber to the distal end of the bypass flow channel, forming a reducing flow channel; and
    at least one guide wall, comprising a proximal portion adjacent to said second flow entrance and a distal portion adjacent to said first flow entrance, said guide wall being angled toward the measurement channel to direct a flow toward the measurement channel.

* * * * *